United States Patent [19]

Yapp et al.

[11] Patent Number: 4,735,614
[45] Date of Patent: Apr. 5, 1988

[54] CATHETER FOR INTRAVASCULAR USE

[75] Inventors: John V. Yapp, Camberley; Graham R. Lay, Hook; Thomas Tivendale, Teddington, all of United Kingdom; Robert H. Cameron; Joseph J. Chang, both of Tampa, Fla.

[73] Assignee: Critikon, Ltd, England

[21] Appl. No.: 831,534

[22] Filed: Feb. 25, 1986

[30] Foreign Application Priority Data

Mar. 14, 1985 [GB] United Kingdom ............... 8506627

[51] Int. Cl.[4] ............................................. A61M 5/18
[52] U.S. Cl. ..................................... 604/165; 604/169
[58] Field of Search ..................... 604/165, 169, 113

[56] References Cited

U.S. PATENT DOCUMENTS

| 2,669,233 | 2/1954 | Friend | 604/113 |
| 3,856,020 | 12/1974 | Kovac | 604/169 |
| 4,126,133 | 11/1978 | Schwartz | 604/169 |

FOREIGN PATENT DOCUMENTS

| 2845643 | 4/1980 | Fed. Rep. of Germany | 604/169 |
| 575559 | 8/1924 | France | 604/169 |

Primary Examiner—C. Fred Rosenbaum
Assistant Examiner—Gene B. Kartchner
Attorney, Agent, or Firm—Donal B. Tobin

[57] ABSTRACT

An improved catheter assembly is provided wherein a cannula depends from a catheter body having a first passageway therethrough communicating with the cannula through which an introducer needle may be introduced and removed. The assembly is provided with a second passageway communicating with the cannula through which a fluid may be introduced. A moveable means is provided disposed across the first passageway and moveable from a first position to a second position. The moveable means is provided with a duct passing therethrough, the duct being coaxial with the first passageway when the moveable means are in a first position to allow the introduction of removal of the introducer needle. Thereafter, the moveable means are adapted to be moved into a second position in which the access of the duct is displaced to be non-coaxial with the first passageway, and hence out of communication therewith and with the moveable means in the catheter body cooperating to seal the duct from the first and second passageways.

22 Claims, 7 Drawing Sheets

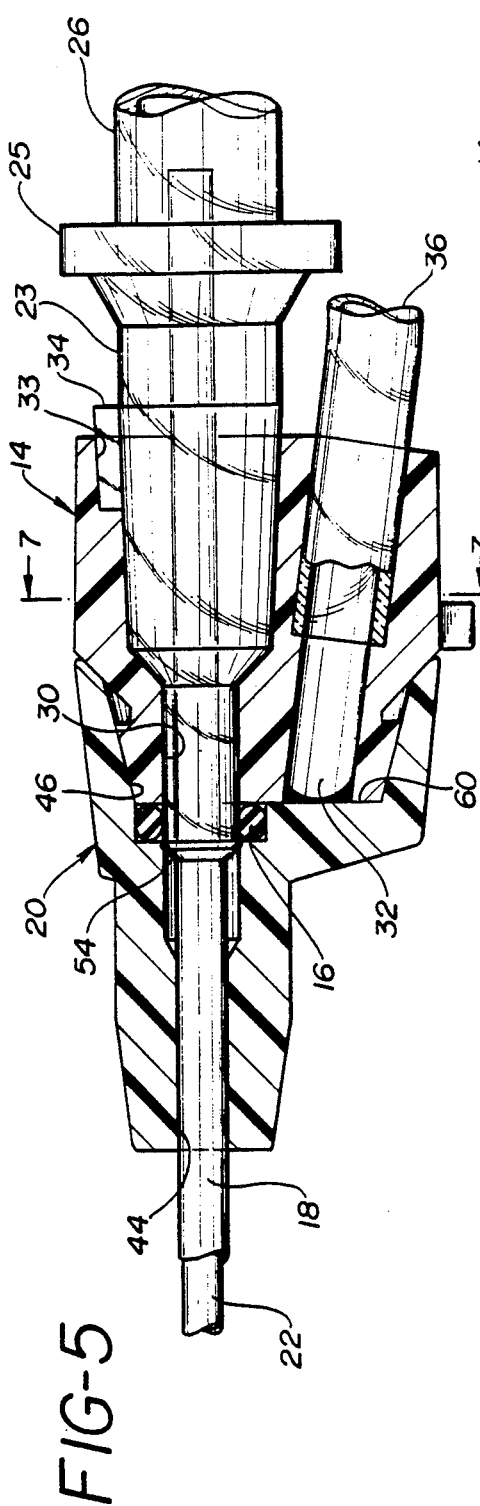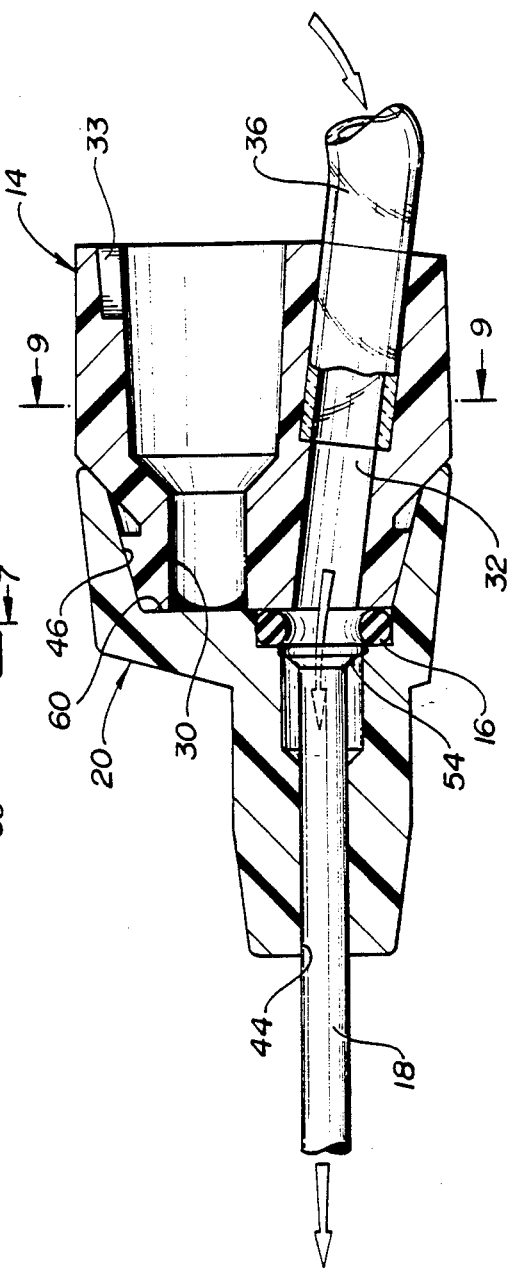
FIG-5
FIG-6

CATHETER FOR INTRAVASCULAR USE

BACKGROUND OF THE INVENTION

This invention relates to catheter assemblies for intravascular, i.e., I.V., use.

Several different types of I.V. catheter assemblies are commercially available. Typically, such catheter assemblies provide a hollow flexible cannula extending from the assembly and coaxial with a first passageway within the assembly. Fluid, to be introduced into the blood vessel, is passed through the first passageway and through the cannula. It is customary to insert the distal end of the cannula into the blood vessel with an introducer needle which initially resides within the cannula and which is withdrawn as the latter is properly seated in the blood vessel. Accordingly, when the cannula is to be inserted, the assembly is provided with the introducer needle in place, i.e., with the needle passing through the first passageway, through the cannula and having the piercing end of the needle protruding from the distal end of the cannula. The blood vessel is pierced and the cannula is inserted into the vessel. The needle must now be withdrawn and the assembly must be placed into flow communication with the fluid to be administered.

These multiple operations have proven to be awkward to perform using conventional catheter assemblies and have frequently resulted in difficulties for both the user and the patient. Often, in the course of these manipulations, the cannula dislodges from the blood vessel and must be reintroduced. The steps of removing the needle and introducing administered fluid into flow communication with the cannula have resulted in spillage of both the administered fluid and the patient's blood.

An attempt to simplify the process is represented by a series of suggestions in which the catheter assembly is provided with a second passageway, ultimately in flow communication with the cannula and, at least in part, independent of the first passageway through which the needle resides during catheter introduction. Representative of such suggestions are those disclosed in U.S. Pat. Nos. 4,496,368; 4,020,835; 4,224,943; 4,326,519; 4,314,555; 4,073,297; 4,079,738; 4,311,137; European Patent Applications Nos. 78300235.5 (publication No. 0.000831); 81300238.3 (publication No. 0.034879) and U.K. Pat. Nos. 1,476,643; 2,088,215 and 1,284,537. Typically, these suggestions comprises a branch or arm having the second passageway therethrough and extending from the catheter assembly at an angle with the axis of the first passageway. The distal end of this branch is in flow communication with the distal portion of the first passageway and hence in communication with the cannula. The proximal end of the branch is generally capped or sealed with a piercable elastomeric self-sealing plug. In operation, the catheter assemblies of this type, with the introducer needle in place, may be first primed with the fluid to be administered, i.e., the second passageway is placed in flow communication with a source of the fluid and filled with the same. The cannula is next introduced into the blood vessel and the introducer needle withdrawn thereby allowing fluid to flow through the second passageway and through the cannula. To prevent fluid from flowing proximally through the first passageway the proximal end of the first passageway is typically provided with a so-called self-sealing elastomeric plug through which the introducer needle may pass for introduction and removal.

While the above described system represents an improvement over the prior awkward systems first described, several drawbacks have been encountered. Firstly, while the prevention of unintended flow and contamination is dependent upon the ability of the self-sealing plug to seal upon removal of the needle, the smooth operation of the insertion of the needle and its removal requires the needle to be easily reciprocated axially through the seal. These contrary requirements, calling for both a loose and a tight fit about the needle at the seal point, must be resolved in favor of a tight fit for patient safety reasons and hence have made manipulation of the needle difficult.

In an effort to resolve this problem, rather complex designs have been suggested for providing a relatively loosely fitting resilient seal about the needle during venipuncture and then means for applying force to the seal after the needle has been removed to close the seal. Such designs are illustrated in the aforementioned U.S. Pat. Nos. 4,311,137 and 4,496,348. Needless to say, the complexity of these designs have greatly added to the cost and difficulty of manufacturing such catheter assemblies and have also added to the number of manipulations required in using the assemblies.

Accordingly, there is a need for a simple, inexpensively manufactured catheter assembly which may be more efficiently utilized for I.V. infusion.

SUMMARY OF THE INVENTION

In accordance with the teachings of this invention, an improved catheter assembly is provided which may be inexpensively produced and employed without the cumbersome manipulations required of heretofore suggested assemblies. Specifically, this invention is directed toward improvements in a catheter assembly of the kind having a cannula depending from the distal end of a catheter body, said body having a first passageway communicating with the cannula through which an introducer needle may be introduced and removed. The assembly is further provided with a second passageway for communicating with said cannula through which a fluid may be introduced.

In accordance with this invention, the assembly is further provide with moveable means disposed across the first passageway, said moveable means being moveable from a first position to a second position. The moveable means are provided with a duct passing therethrough, the duct being coaxial with the first passageway when the moveable means are in the first position to allow the introduction and removal of the introducer needle. Upon removal of the needle after venipuncture, the moveable means are adapted ot be moveable into the second position in which the axis of the duct is displaced to be non-coaxial with the first passageway and hence out of fluid communication therewith and with the moveable means and the catheter body cooperating to seal the duct from the first and second passageways.

In one embodiment, the second passageway is provided with a port at its distal end which communicates with the first passageway at a point between the moveable means and the cannula. The moveable means are provided with an occlusive wall which seals the first passageway when the moveable means are in the second position.

It should be noted that as used herein, the term "occlusive wall" is meant to denote a wall which, when inserted into a passageway or flow path, acts to occlude the flow of liquid. Preferably, such occlusive wall does not occlude the flow of gas so that a passageway upstream of the wall may be primed and displaced air may be vented. This can easily be accomplished by an occlusive wall which leaves a gap of the order of magnitude of 0.1 mm or less, which gap is small enough to impede the flow of liquid but will allow the passage of gas.

In a second embodiment, the moveable means are provided between the second passageway and the first passageway. The movable means are provided with an occlusive wall which seals the second passageway from the first passageway when the moveable means are in the first position. The moveable means are further provided with a second duct which communicates with the first passageway and the second passageway when the moveable means are in the second position. In a form of this embodiment, the second passageway comprises the second duct in the moveable means; the second duct being non-communicating with the first passageway when the movable means are in the first position and the second duct being in fluid communication with the first passageway when the moveable means are in the second position.

It will be appreciated that the simplicity and ease of manipulation of this improved catheter assembly is based upon the concept of translating the axis of the duct in the moveable means from a coaxial position with the first passageway to a non-coaxial position. Preferably, the axis of the duct is translated into a position non-coaxial, but parallel, to the axis of the first passageway. This translation may be accomplished simply by providing gripping means, externally accessible, to move the moveable means from the first position (coaxial) to the second position (non-coaxial). Such movement may be accomplished by rotating the movable means with respect to the catheter body or by reciprocating the moveable means from the first position to the second position.

In one embodiment, the gripping means comprise a tab extending from the moveable means when the moveable means are in the first position. The tab may simply be pushed into the catheter assembly to reciprocate the moving means into the second position.

In another embodiment, the gripping means may comprise a wing extending from the moveable means which wing may be gripped and rotated in a plane of rotation normal to the axis of the assembly to move the moveable means into a second position. A preferred embodiment is provided wherein a second wing extends from the catheter body and may also be gripped and rotated so that by rotating both wings the moveable means are rotated relative to the catheter body into the second position. The wings may thereafter serve as surfaces for taping the catheter assembly in place on the patient's body. This embodiment economically and efficiently combines the functions of second passageway catheter assemblies with those of winged catheter assemblies such as are known in the art.

BRIEF DESCRIPTION OF THE DRAWINGS

FIG. 5 is a longitudinal cross-sectional view of a portion of the catheter assembly of FIG. 1, taken along line 5—5 of FIG. 1;

FIG. 6 is a longitudinal cross-sectional view of a portion of the catheter assembly of FIG. 2, taken along line 6—6 of FIG. 2;

DETAILED DESCRIPTION OF THE INVENTION

Figure 1:
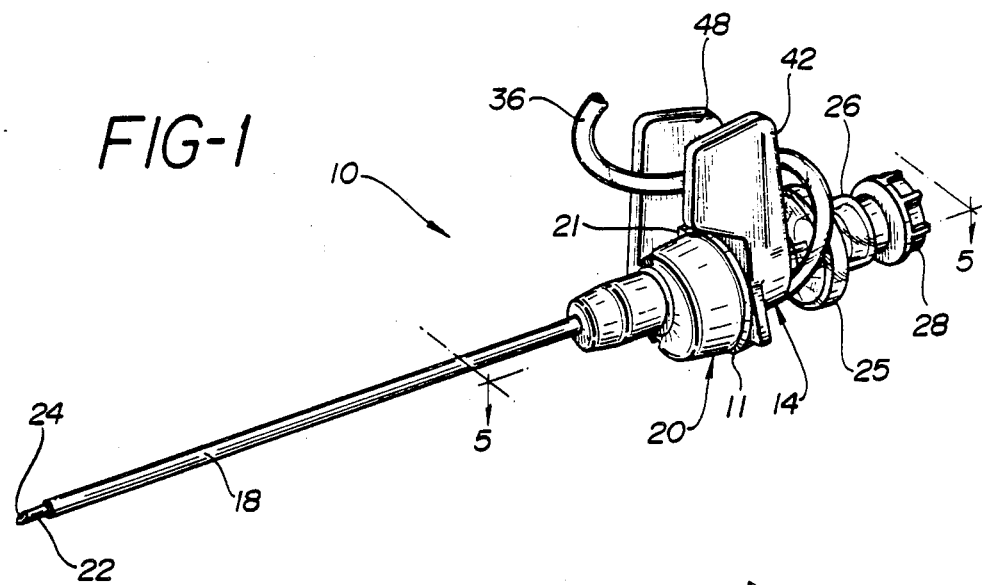
FIG. 1 is a perspective view of a preferred embodiment of the catheter assembly of this invention shown with the moveable means in the first position and with the introducer needle in place for venipuncture.

Referring now to FIGS. 1–9, illustrated therein is a preferred embodiment of the catheter assembly 10 of this invention. As used herein the term "proximal" shall mean the direction toward the user whereas the term "distal" shall mean the direction away from the user and toward the patient. As best viewed in FIG. 3, the assembly comprises an introducer needle sub-assembly 12, a moveable means 14, a sealing ring 16, a cannula 18 and a catheter body 20.

The introducer needle sub-assembly comprises an introducer needle 22 having a sharp piercing distal end 24 and fitted at its proximal end with a visible flash chamber 26 and a flash plug 28. The needle 22 is secured at its proximal end into a needle hub 23 which is provided with an enlarged cross-section 25 for gripping by the user.

The moveable means 14 comprises a body having a first duct 30 adapted for receiving the introducer needle 22. As best viewed in FIGS. 5 and 6, the first duct 30 has an enlarged proximal portion for accommodating the distal portion of needle hub 23. Additionally, the enlarged portion of the first duct 30 is provided with a depression 33 adapted to receive a projection 34 on the needle hub to insure the maintaining of proper rotational orientation of the needle.

A second duct or passageway 32 is provided in this embodiment in the moveable means, the proximal end of said second duct being in flow communication with the source of administered fluid e.g., by way of flexible tubing 36. As illustrated, flexible tubing 36 may be provided with dual introduction ports with one port 38 having, for example, a standard Luer connection for coupling to an I.V. set and with the other port 40 having a flexible rubber diaphragm to allow for intermittent injection of liquids into tube 36.

Extending from the moveable means 14 is a gripping means in the form of a first wing 42 which the user may employ to rotate the moveable means from a first to a second position as will be described in further detail hereinafter.

The catheter body 20 is provided at its distal portion with a first passageway 44 through which both the needle and the administered liquid communicate with the cannula 18 of the assembly. The proximal portion of the catheter body 20 is provided with an enlarged bore 46 adapted to receive the distal end of the moveable means 14.

The catheter body 20 is also provided with a second wing 48 adapted to be gripped and rotated in a direction counter to the rotation of the first wing 42 of moveable means 14 to rotate said moveable means with respect to catheter body 20 from a first to a second position. Wing 48 is conveniently provided with a channel 50 and a pair of flexible brackets 52 and 53 for supporting the tubing 36, as may be best viewed in FIGS. 2, 7, 8 and 9.

The flexible cannula 18 is provided with a metal spigot 54 at its proximal end. As can be best seen in FIGS. 4, 5 and 6, when the catheter assembly is assembled, the cannula 18 extends distally through first passageway 44 with spigot 54 pressing the wall of cannula 18 into a friction fit with the wall of first passageway 44. The elastomeric sealing ring 16 then rests on the proximal opening of the cannula 18.

Figure 4:
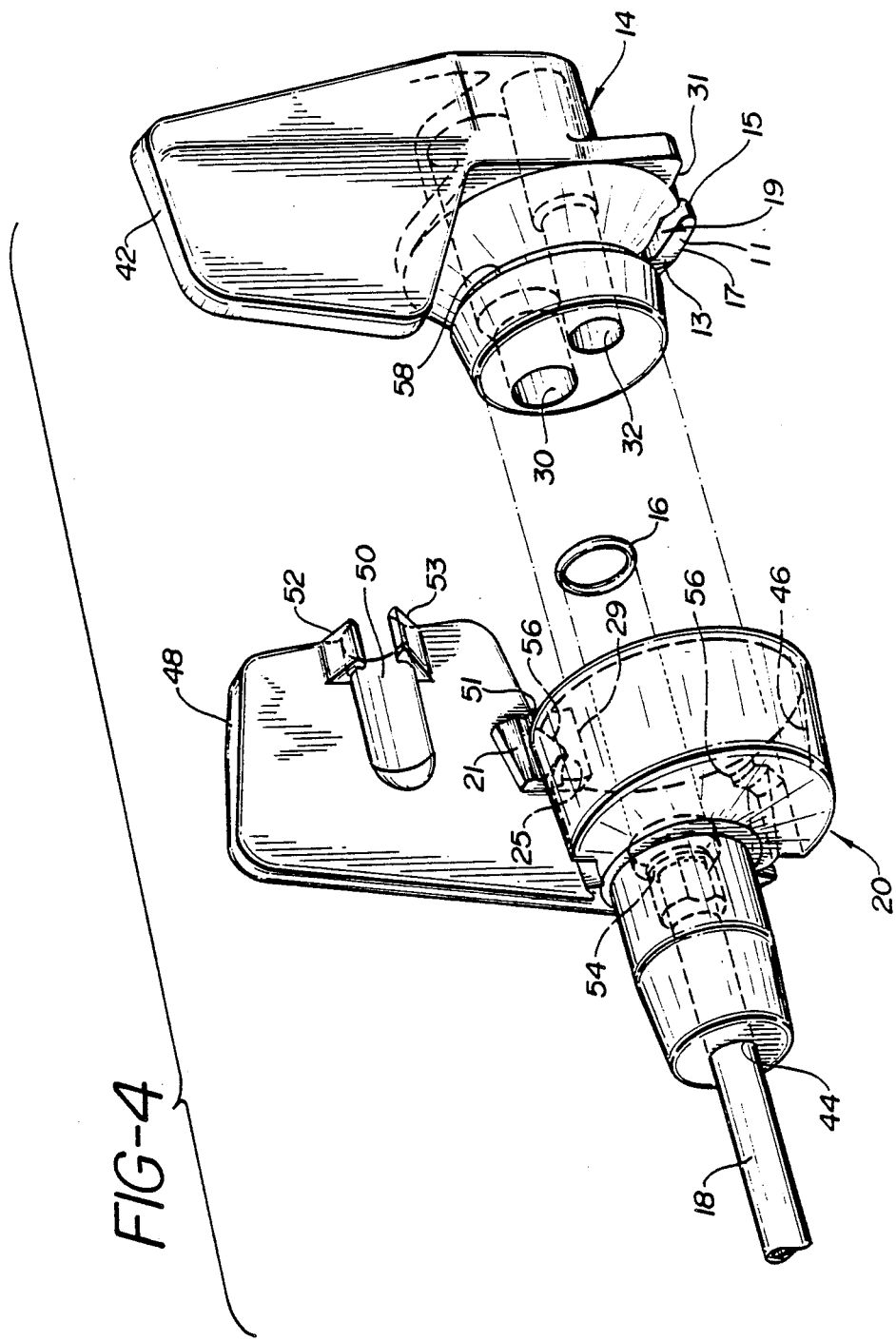
FIG. 4 is a partially exploded perspective view of the catheter assembly of FIG. 1.

As best seen in FIGS. 4–6, the distal portion of moveable means 14 is received within the enlarged bore 46 of the catheter body 20 with the distal face of the moveable means abutting the proximal opening of passageway 44 and pressing down on sealing ring 16. The moveable means 14 and the catheter body 20 are held in this position by the cooperation of spurs 56, which project inwardly, from the walls of the enlarged bore 46, cooperating with a circumferential channel 58 in the peripheral surface of moveable means 14. As moveable means 14 and catheter body 20 are assembled, spurs 56 snap into channel 58 and hold these two elements together.

Figure 7:
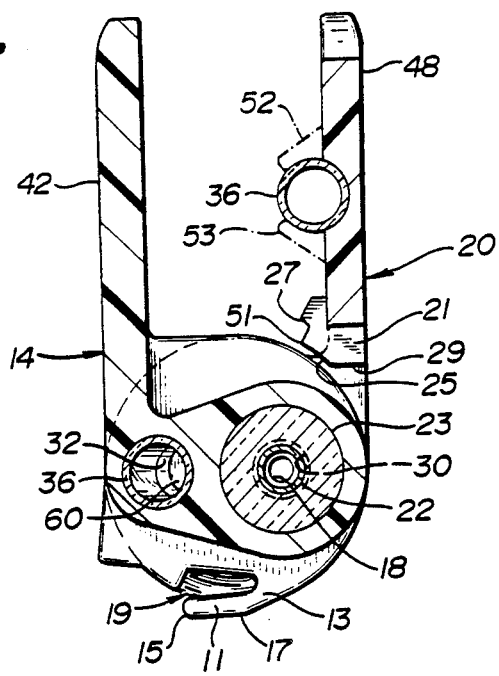
FIG. 7 is a transverse cross-sectional view of FIG. 5, taken along line 7—7 of FIG. 5.

With the moveable means in its first position (as shown in FIGS. 1, 5, and 7) i.e., with the wings 42 and 48 closed, the first duct 30 in moveable means 14 is coaxial with first passageway 44 in catheter body 20 and thus allows introducer needle 22 to pass through these ducts and into cannula 18. As can be seen in FIG. 1, with the introducer needle 22 fully seated within the assembly, its distal tip extends slightly beyond the distal end of the cannula 18. As can be best viewed in FIG. 5, in this position, the second passageway or duct 32 in moveable means 14 is sealed by virtue of the cooperation between the moveable means and the catheter body. Specifically, the wall 60 which is the distal end of enlarged bore 46 occludes the distal end of duct 32. Accordingly, duct 32 (which leads to the two introduction ports 38 and 40) is sealed and is not in fluid communication with either first passageway 44 or first duct 30.

The catheter assembly, in the first position of the moveable means as illustrated in FIGS. 1, 5 and 7 (i.e., with wings 42 and 48 closed) is ready to be used. The introducer needle 22 and cannula 18 combination is introduced into a blood vessel. As is customary with I.V. catheters, when the flash chamber 26 shows blood and with the cannula 18 in the blood vessel, the introducer needle 22 is gradually withdrawn from the assembly as the cannula 18 is advanced into the blood vessel. It will be appreciated that the closed pair of wings 42, 48 provide a convenient purchase between the thumb and forefinger of one hand of the user. This, together with the purchase on the enlarged cross-section 25 of the flash chamber provided to the other hand, gives a positive and safe mode to enable the cannula to be correctly seated in the blood vessel and the introducer needle 22 fully removed. It will also be appreciated that the first duct 30 in the moveable means is only truly coaxial with the first passageway 44 in the catheter body when the two wings 42, 48 are folded strictly parallel to one another. If the wings are pressed slightly closer together this causes these two ducts to try to move out of coaxial alignment, with the result that the intervening needle 22 is firmly wedged relative to the two elements. This facility to press slightly on the wings enables the position of the introducer needle 22 relative to cannula 18 to be retained firmly, which can also assist in manipulation of the catheter.

Figure 2:
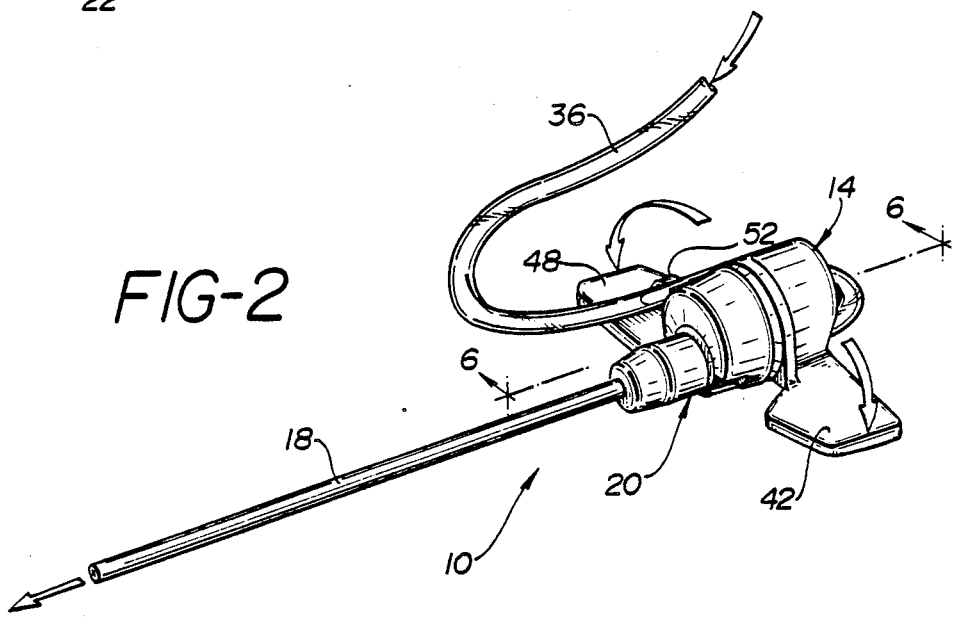
FIG. 2 is a perspective view of the catheter assembly of FIG. 1 with the moveable means in the second position, the needle removed and a source of fluid in flow communication with the cannula.
Figure 3:
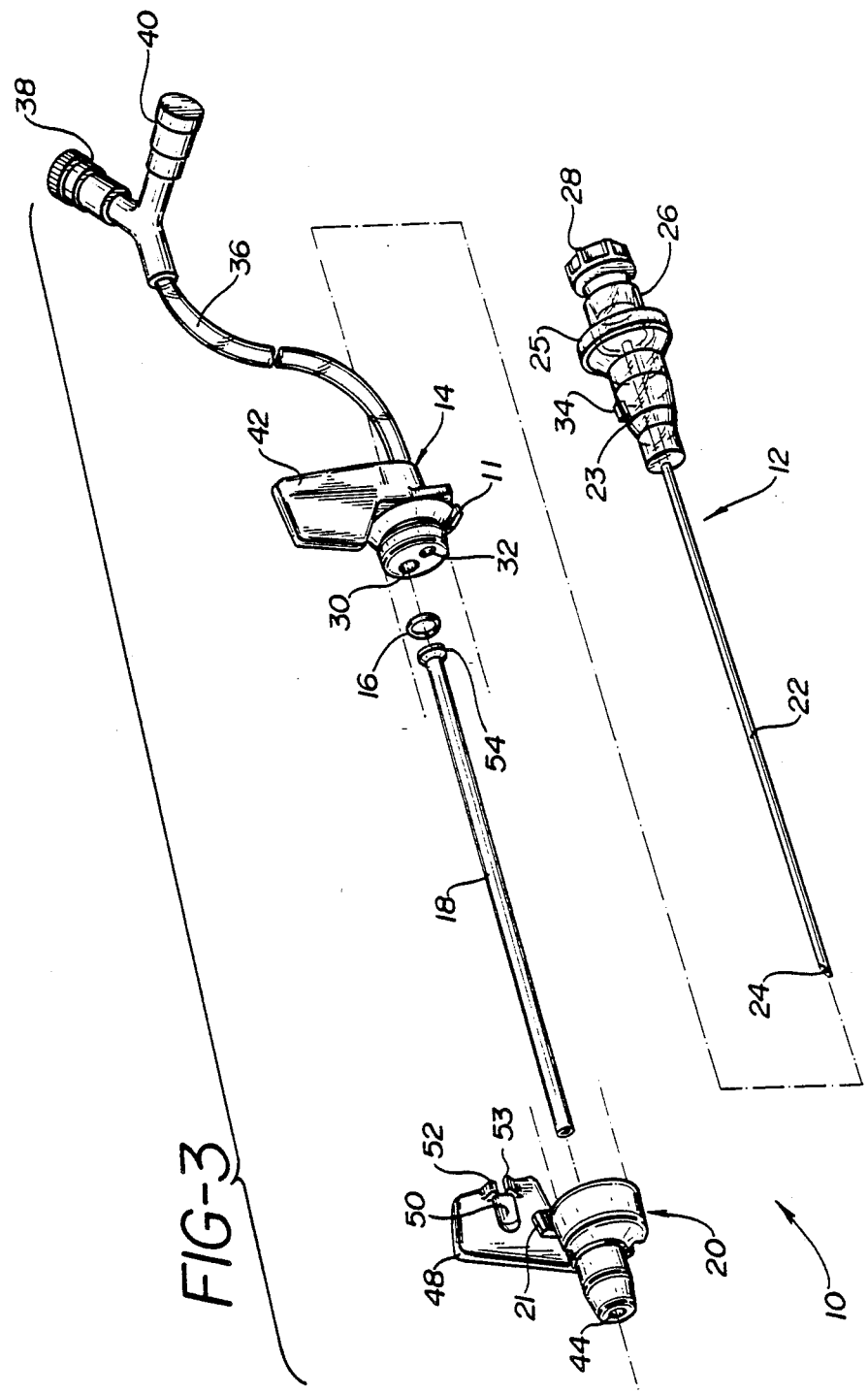
FIG. 3 is an exploded perspective view of the components of the catheter assembly in the position of FIG. 1.
Figure 9:
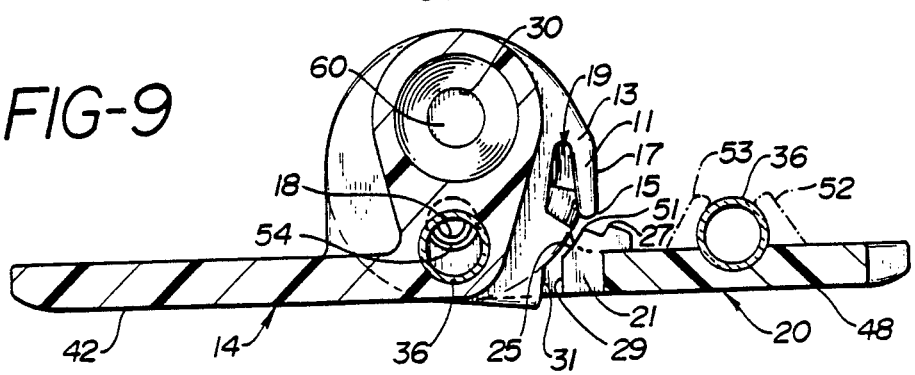
FIG. 9 is a transverse cross-sectional view of FIG. 6, taken along line 9—9 of FIG. 6.

Once the introducer needle 22 has been withdrawn, the moveable means 14 may be placed in the second position by the user's gripping each of the wings 42 and 48 and rotating each of them, counter to each other, 90° whereby moveable means 14 will be rotated, with respect to catheter body 20, 180°. The catheter assembly in this second position is illustrated in FIGS. 2, 6 and 9. As best viewed in FIGS. 6 and 9, one effect of this rotation is to translate the first duct 30 of the moveable means from a coaxial position with the first passageway 44 in catheter body 20 (as in FIG. 5) to a non-coaxial position (FIG. 6). In this second position, it should be noted that the moveable means 14 and the catheter body 20 cooperate to seal the duct 30 from communication with both the first passageway 44 in catheter body 20 and the second passageway or second duct 32 in the moveable means. Specifically, this is accomplished by occluding the distal end of duct 30 with wall 60 of the catheter body.

Further, the relative rotation of the moveable means 14 with respect to the catheter body 20 now places the first passageway 44 in the catheter body into fluid communication with the second duct 32. This enables fluids to be introduced into the blood vessel from the ports 38 and 40.

Figure 8:
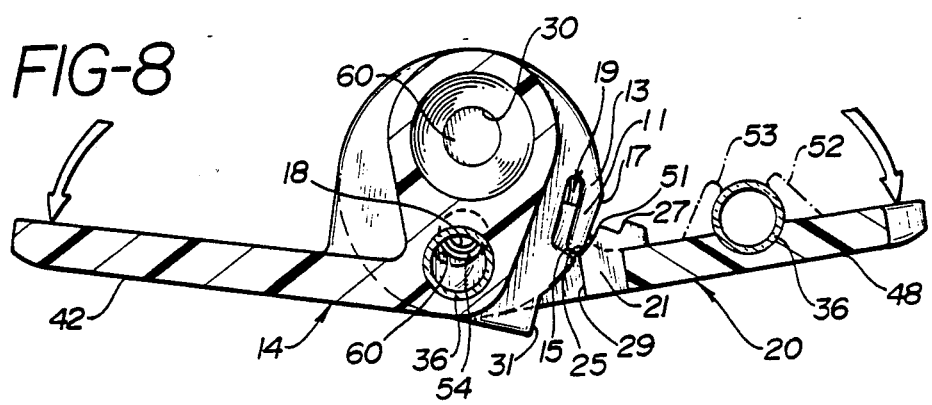
FIG. 8 is a transverse cross-sectional view of the catheter assembly of FIG. 1 and similar to that of FIG. 7, with the exception that the assembly is illustrated in a position intermediate to that of the first and second positions.

Referring now to FIGS. 7, 8 and 9, (illustrating the assembly in, respectively, the first, intermediate, and second positions of the moveable means 14) it can be seen that the assembly has been provided with rotation limiting means. Specifically, the outer peripheral surface of the moveable means has been provided with a flexible arm 11, integral with the moveable means at a first end 13 and biased to have the second end 15 pivoted away from the moveable means. Arm 11 has sufficient flexibility so that when force is applied to its outer surface 17, arm 11 may be urged against the periphery of the moveable means. The periphery of the moveable means is provided with a recess 19 to accommodate arm 11 so that when force is applied to surface 17, arm 11 may be urged into recess 19 and then surface 17, in combination with the peripheral surface of the moveable means, presents a smooth surface of rotation. Arm 11 is located on the moveable means in a plane of rotation proximal to the proximal end of catheter body 20 when the unit is assembled.

Wing 48 of catheter body 20 is provided with a rotation limiting projection 21. The projection 21 is located so as to lie in the same plane of rotation as arm 11 when the unit is assembled. The trailing edge 51 of projection 21 is positioned in said plane at essentially 180° from the second end 15 of arm 11 when the assembly is in the first position and is rotated to a co-angular position when the assembly is in the second position. Projection 21 is also provided with a concave surface 25 which rotates essentially concentrically with the peripheral surface of the moveable means.

As the wings 42 and 48 are counter rotated from the first position (FIG. 7) through the intermediate position (FIG. 8) it can be seen that the projection 21 approaches the arm 11. In FIG. 8, the relative rotation has reached the point where surface 25 of projection 21 now imposes force on surface 17 of arm 11, thus forcing arm 11 into recess 19 and allowing continued rotation.

In FIG. 9, the wings have been fully rotated in the second position wherein surface 25 of projection 21 has been rotated just past second end 15 of arm 11 and no longer exerts force against surface 17. Accordingly, the biased arm 11 now moves away from the periphery of the moveable means and into an interfering position with projection 21 thus precluding rotation of the wings back into the first position. To insure that, in this position, end 15 of arm 11 positively interfers with the projection 21, a shoulder 27 is provided in edge 51 of projection 21 to accommodate end 15.

It should be noted from FIG. 9 that rotation much beyond the second position is limited by the ends 29 and 31 of wings 48 and 42 respectively bearing against each other to prevent such excess rotation. Some rotation after the wings have been rotated into the second position is desirable, however, to enable the wings to take up the contours of the patient's body. Accordingly, end 15 of arm 11 is positioned with respect to end 31 of wing 42 so as to allow about nine degrees of rotation of one wing with respect to the other when in the second position. Such small misalignment is insufficient to alter the desired flow path of liquid through the catheter assembly.

The fully opened wings 42, 48 can be secured to the patient with surgical tape, with the flexible tube 36 being held in channel 50 by brackets 52 and 53. By so holding the tube, a torque imposed upon the flexible tube is prevented from being transmitted to the cannula where it might otherwise adversely effect the position of the cannula in the blood vessel.

The above described embodiment, utilizing rotatable wings as gripping means for the moveable means, provides the user with many advantages as have been noted herein. It will be understood, however, that the principles of this invention, notably the translation of the axis of a duct in a moveable means from coaxial to non-coaxial positions, may be embodied in a wide variety of catheter assemblies and that such various assemblies are contemplated to be encompassed by this invention.

Figure 10:
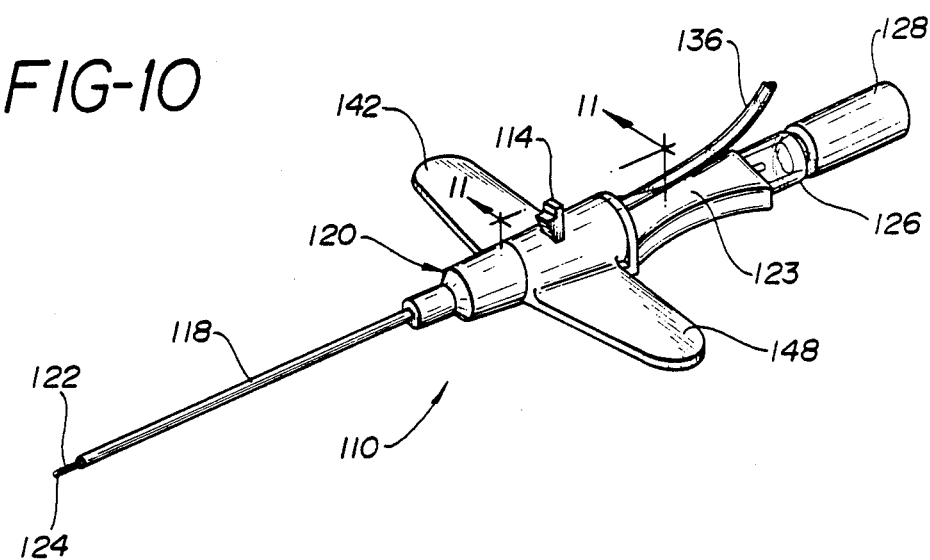
FIG. 10 is a perspective view of a second embodiment of a catheter assembly of this invention illustrated with the moveable means in the first position and with the introducer needle in place.
Figure 11:
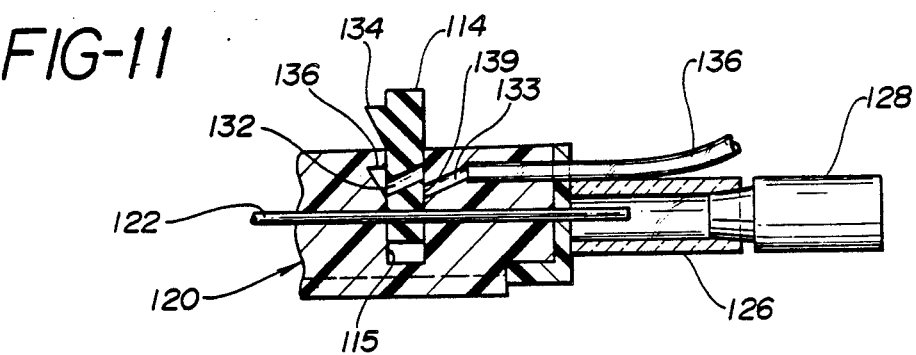
FIG. 11 is a partial longitudinal cross-sectional view of the catheter assembly of FIG. 10 taken through line 11—11.
Figure 12:
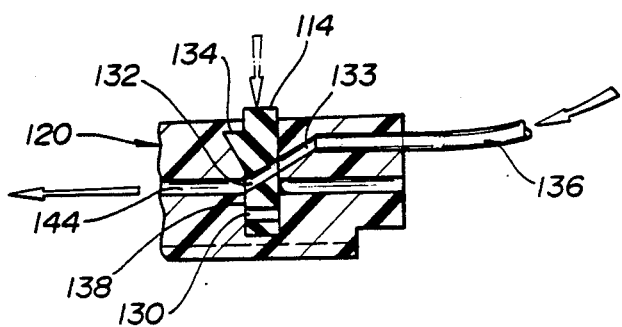
FIG. 12 is a partial longitudinal cross-sectional view of the catheter assembly of FIG. 10 illustrated with the moveable means in the second position.

One such alternative embodiment is illustrated in FIGS. 10 through 12. Again, the catheter assembly 110 comprises a needle sub-assembly consisting of a flash chamber 126, a flash plug 128, a needle hub 123 having a gripping portion 125 and an introducer needle 122 having a sharp piercing distal end 124.

A catheter body 120 is provided from which cannula 118 depends and is in flow communication with a first passageway 144 within the catheter body. The catheter body is also provided with laterally extending wings 142 and 148 which provide taping surfaces for securing the assembly to the patient's body but, unlike the prior embodiment, need not be rotatable. A second passageway 133 is provided in catheter body and adapted to be in flow communication with a source of administered fluid via flexible tube 136.

Moveable means 114 is provided in this embodiment in the form of a shutter, and is adapted to be moved from a first position, as illustrated in FIGS. 10 and 11, to a second position, as illustrated in FIG. 12, by reciprocating in a slot 115 provided in the catheter body 120. Moveable means 114 is provided with a first duct 130 which in the first position is coaxial with the first passageway 114 in the catheter body 120. This allows the introduction and removal of the needle 122 through the proximal end of catheter body 120, through the first duct 130, through the first passageway 144, through the cannula 118 and finally protruding through the distal end of the cannula 118 as is illustrated in FIG. 10. Moveable means 114 is also provided with an occlusive wall 139 which, when in the first position, occludes the distal end of second passageway 133 and thereby prevents flow communication between passageway 133 and the other ducts and passageways. Additionally, moveable means 114 is provided with a second duct 132 adapted to communicate between the second passageway 133 and the first passageway 144 when moveable means is in the second position.

Accordingly, with the assembly 110 in the first position illustrated in FIGS. 10 and 11, venipuncture may be accomplished and the cannula may be placed within the blood vessel with the needle sub-assembly withdrawn, as has been described hereinabove.

The moveable means 114 may now be reciprocated in slot 115 into its second position as illustrated in FIG. 12 (the arrow indicating the direction of reciprocation). In this position, duct 132 now communicates between first passageway 144 and second passageway 133 and, accordingly, allows flow of administered fluid to the cannula.

It should be noted that, by reciprocating moveable means into its second position, the axis of duct 130 has been translated from a coaxial relationship with respect to first passageway 144 to a non-coaxial relationship. It will also be noted that in this second position, the moveable means and the catheter body cooperates to occlude the distal end of duct 130. Specifically, occluding wall 138, in this case the wall of the slot 115, occludes the distal end of duct 130 and prevents duct 130 from being in flow communication with the other passageways.

To facilitate the operation of the assembly, moveable means 114 is adapted to project a gripping (or pushing) surface above the periphery of the catheter body. Preferably the gripping surface is essentially flush with the periphery of the catheter body when the assembly is in the second position. Further, to insure secure positioning in the second position, moveable means is provided with a spur 134 which cooperates with an indent 136 in the walls of slot 115 to maintain moveable means in the second position.

The embodiment illustrated in FIGS. 10 through 12 depicts the moveable means positioned between the first and second passageway of the catheter body. In contrast thereto, the embodiment illustrated in FIGS. 13 through 15 is provided to illustrate the positioning of the second passageway between the first passageway and the moveable means.

Figure 13:
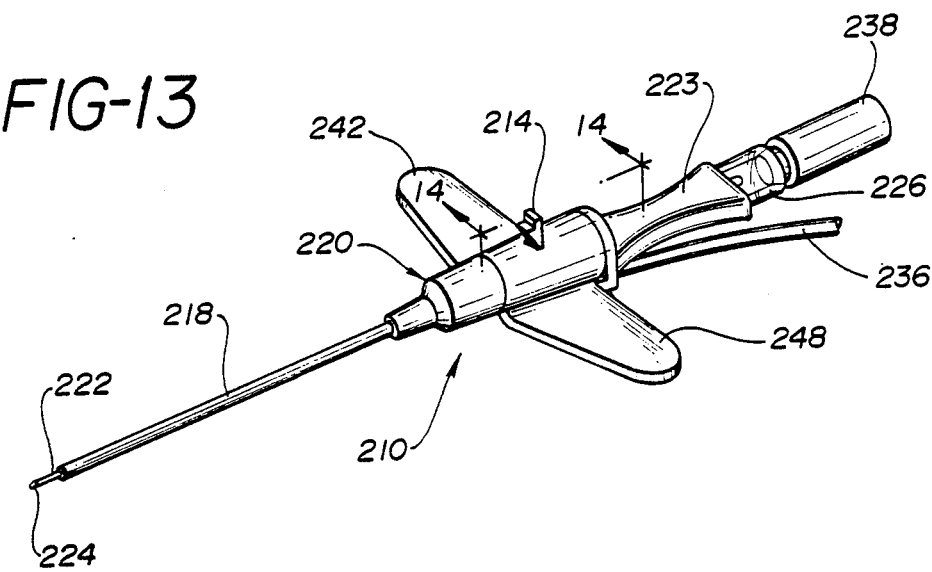
FIG. 13 is a perspective view of a third embodiment of the catheter assembly of this invention illustrated with the moveable means in the first position and with the introducer needle in place.
Figure 14:
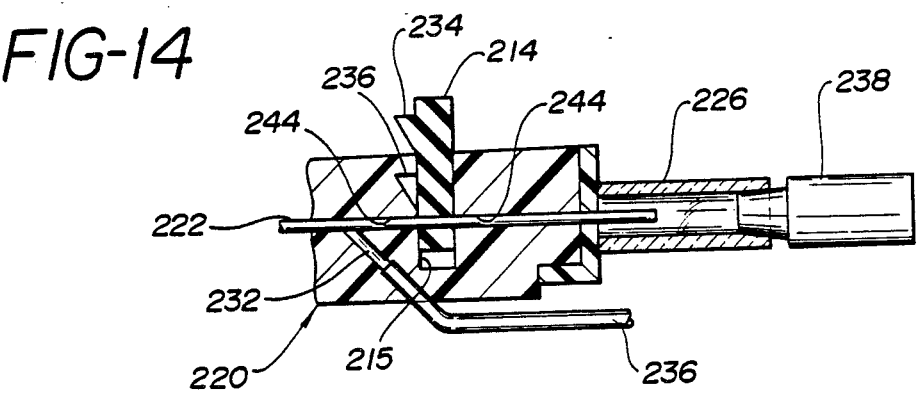
FIG. 14 is a partial longitudinal cross-sectional view of the catheter assembly of FIG. 13, taken through line 14—14.
Figure 15:
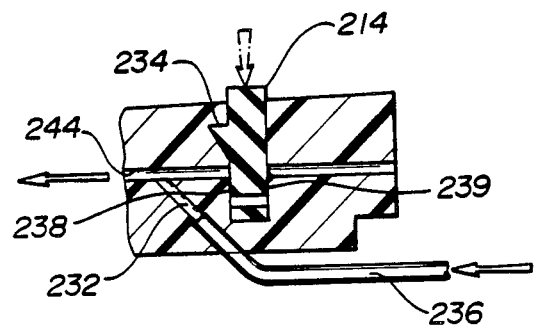
FIG. 15 is a partial longitudinal cross-sectional view of the catheter assembly of FIG. 13 illustrated with the moveable means in the second position.

Referring to FIGS. 13 through 15, the catheter assembly 210 again comprises a needle sub-assembly consisting of a flash chamber 226, a flash plug 228, a needle hub 223 having a gripping portion 225 and an introducer needle 222 having a sharp piercing end 224.

Catheter body 220 from which cannula 218 depends is provided with a first passageway 244 and with a second passageway 233 adapted to be in flow communication with administered fluid via flexible tube 136. The second passageway communicates with the first passageway 244 via port 231.

Moveable means 214 is provided, again in the form of a shutter reciprocating in a slot 215 provided in the catheter body 220. In this embodiment, however, the slot is positioned proximally with respect to the port 231. Moveable means 214 is provided with a duct 230 which, in the first position is coaxial with the first passageway 244 allowing the introduction and removal of needle 222. It should be noted that flow through the second passageway 232 may be prevented during introduction and removal of the needle by occluding the flexible tube 234 by means well known but not shown in the drawings.

Having accomplished venipuncture, placed the cannula into the blood vessel and removed the needle sub-assembly, the moveable means 214 may now be reciprocated into its second position as described in connection with the prior embodiment. In this position, illustrated in FIG. 15, the axis of the duct 230 has again been translated from coaxial relationship with respect to the first passageway to non-coaxial relationship. Again, the catheter body and the moveable means cooperate to occlude the duct. Specifically, occlusive wall 238 of slot 215 occludes the distal end of duct 230. It should be noted that the proximal end of passageway 244 is also occluded by cooperation between the moveable means and the catheter body. In this case, occlusive wall 239 of moveable means 214 occludes the proximal end of first passageway 244 and prevents proximally direct flow.

The materials used to manufacture the devices described herein may be any of the suitable medically acceptable plastics except that generally the introducer needles and spigots are preferably stainless steel. For example, the cannulas may be of polytetrafluoroethylene and the remaining elements of polystyrene. Advantageously components which carry liquids are transparent or translucent so that such liquid transport may be visible.

What is claimed is:

1. In a catheter assembly having a catheter body, a cannula depending from said catheter body and a first passageway in said catheter body communicating with the cannula through which an introducer needle may be introduced and removed; said catheter assembly having a second passageway for communicating with said cannula through which a liquid may be introduced; the improvement comprising:

moveable means disposed in confronting relationship to said first passageway, and rotatably secured to said catheter body, said means being moveable from a first position to a second position by rotating said moveable means with respect to said catheter body said rotation being in a plane normal to the linear axis of said first and second passageways;

said moveable means provided with a first duct passing therethrough, said first duct being coaxial with said first passageway when said moveable means are in said first position to allow the introduction and removal of said introducer needle; and said moveable means being moveable into said second position in which the axis of said first duct is displaced to be non-coaxial with the first passageway and out of fluid communication therewith, the axis of said first duct in its displaced position remaining substantially parallel to the axis of said first passageway.

2. The catheter assembly of claim 1 wherein, when said moveable means are in said second position, said catheter body and said moveable means cooperate to seal said first duct from said first passageway.

3. The catheter assembly of claim 2 wherein said catheter body is provided with an occlusive wall adapted to seal said first duct from said first passageway when said moveable means are in such second position.

4. The catheter assembly of claim 1 wherein when said moveable means are in said second position, said catheter body and said moveable means cooperate to seal said first duct from said second passageway.

5. The catheter assembly of claim 4 wherein said catheter body is provided with an occlusive wall adapted to seal said first duct from said first passageway when said moveable means are in said second position.

6. The catheter assembly of claim 1 wherein when said moveable means are in said second position, said catheter body and said moveable means cooperate to seal said first duct from said first and second passageways.

7. The catheter assembly of claim 1 wherein when said moveable means are in said first position, said catheter body and said moveable means cooperate to seal said first passageway from said second passageway.

8. The catheter assembly of claim 7 wherein said catheter body is provided with an occlusive wall adapted to seal said first passageway from said second passageway when said moveable means are in said first position.

9. The catheter assembly of claim 7 wherein said moveable means are provided with an occlusive wall adapted to seal said first passageway from said second passageway when said moveable means are in said first position.

10. The catheter assembly of claim 1 wherein said first passageway and second passageway are provided in said catheter body.

11. The catheter assembly of claim 10 wherein said moveable means comprise a second duct for communicating between said first and second passageway when said moveable means are in said second position.

12. The catheter assembly of claim 1 wherein said second passageway comprises a second duct in said moveable means.

13. The catheter assembly of claim 1 wherein said moveable means are provided with gripping means, externally accessible from the assembly, for gripping and rotating said moveable means.

14. The catheter assembly of claim 13 wherein said gripping means comprise a first wing.

15. The catheter assembly of claim 14 wherein said catheter body comprises a second wing for gripping whereby said moveable means may be rotated with respect to said catheter body by gripping and rotating said wings in counter directions with respect to each other.

16. The catheter assembly of claim 15 wherein said moveable means are in said first position when the plane of said wings are essentially parallel and in the second position when said wings are essentially co-planar.

17. The catheter assembly of claim 1 wherein said assembly is provided with rotation limiting means adapted to prevent said moveable means from rotating back to said first position when in said second position.

18. The catheter assembly of claim 1 wherein said moveable means are provided with a gripping means, externally accessible from the assembly, for reciprocating said moveable means.

19. The catheter assembly of claim 1 wherein said moveable means comprise a shutter and said catheter body is provided with a slot in which said shutter may be reciprocated from said first to said second position.

20. The catheter assembly of claim 19 wherein said assembly is provided with reciprocating limiting means adapted to prevent said moveable means from reciprocating back to said first position when in said second position.

21. In a catheter assembly having a catheter body, a cannula depending from said catheter body and a first passageway in said catheter body communicating with the cannula through which an introducer needle may be introduced and removed; said catheter assembly having a second passageway for communicating with said cannula through which a liquid may be introduced; the improvement comprising:

moveable means disposed across said first passageway said moveable means being moveable between a first position and a second position by linear reciprocal motion with respect to said catheter body;

said moveable means provided with a first duct and a second duct passing therethrough, said first duct being coaxial with said first passageway when said moveable means are in said first position to allow the introduction and removal of said introducer needle; and said moveable means being moveable into said second position in which the axis of said first duct is displaced to be noncoaxial with said first passageway and out of fluid communication therewith.

22. The catheter assembly of claim 21 wherein said linear reciprocal motion is in a direction generally transversed to the axis of said catheter body.

* * * * *